United States Patent [19]

DeVries et al.

[11] Patent Number: 5,264,646
[45] Date of Patent: Nov. 23, 1993

[54] PROCESS FOR PREPARING VINYLICALLY-UNSATURATED COMPOUNDS

[75] Inventors: Robert A. DeVries; Gregory F. Schmidt; Hughie R. Frick, all of Midland, Mich.; Bonnie Frick, Administrator of said Hughie R. Frick, deceased

[73] Assignee: The Dow Chemical Company, Midland, Mich.

[21] Appl. No.: 677,023

[22] Filed: Mar. 28, 1991

[51] Int. Cl.$^5$ .................................. C07C 1/30
[52] U.S. Cl. .................................. 585/641; 585/435; 585/638
[58] Field of Search ............... 585/435, 438, 641, 536, 585/638

[56] References Cited

U.S. PATENT DOCUMENTS

| | | | |
|---|---|---|---|
| 3,922,299 | 11/1975 | Heck | 260/476 R |
| 4,142,060 | 2/1979 | Kuntz | 568/840 |
| 4,540,763 | 9/1985 | Kirchhoff | 526/281 |
| 4,622,375 | 11/1986 | Wong | 526/284 |
| 4,759,874 | 7/1988 | Gros | 252/512 |
| 4,812,588 | 3/1989 | Schrock | 556/453 |
| 4,822,930 | 4/1989 | Liu | 570/206 |
| 4,831,172 | 5/1989 | Hahn et al. | 556/419 |
| 4,918,215 | 4/1990 | Reinehr et al. | 558/401 |

FOREIGN PATENT DOCUMENTS 0062608 3/1982 European Pat. Off. .

OTHER PUBLICATIONS

Heck: Pd. catalyzed vinylation of organic halides Organic Reactions 27, 345–390 (1982).
Plevyak et al., J. Org. Chem., "Palladium-Catalyzed Arylation of Ethylene," vol. 43, No. 12, pp. 2453–2456, 1978.
Heck, *Organic Reactions*, vol. 27 (1982) pp. 345–390.
Dieck, et al., *J. Am. Chem. Soc.*, vol. 96, pp. 1133–1136, 1974.
Chemical Abstract 86:55073g, vol. 86, 1977.
Chemical Abstract 96:122005h, vol. 96, 1982.
Swern, *Organic Peroxides*, vol. III, pp. 236–238 (1981).
Chemical Abstract 54:16381g (1960).
Horner et al., "Die Reduktion organischer Peroxyde mit tertiären Phosphinen," *Annalen*, vol. 591 (1955), pp. 138–152.
Petrarch Systems, Inc. "Silicon Compounds Register and Review," 1987, p. 114.

Primary Examiner—Asok Pal
Assistant Examiner—P. Achutamurthy
Attorney, Agent, or Firm—Charlotte M. Kraebel; Charles J. Enright

[57] ABSTRACT

A process for preparing a vinylically-unsaturated product compound comprises reacting a halogenated organic compound with a hydrolytically-stable, vinylically-unsaturated precursor compound in the presence of (a) a homogeneous zerovalent palladium catalyst complex, (b) an organic hydrogen halide acceptor and (c) a diluent, wherein the diluent is water or an aqueous solution containing up to 95% by volume of an organic solvent. The halogenated organic compound is selected from aryl halides, benzyl halides or vinylic halides. The hydrolytically-stable, vinylically-unsaturated precursor compound is selected from organosilicon compounds, hydrocarbon compounds or compounds containing at least one of an oxygen atom, a nitrogen atom, a sulfur atom, a phosphorus atom or a combination thereof.

43 Claims, No Drawings

PROCESS FOR PREPARING VINYLICALLY-UNSATURATED COMPOUNDS

TECHNICAL FIELD

This invention relates to an improved process for the synthesis of vinylically-unsaturated compounds by reaction between halogenated organic compounds and hydrolytically-stable, vinylically-unsaturated precursor compounds.

BACKGROUND ART

The palladium-catalyzed vinylation of organic halides has been reviewed by Heck, *Organic Reactions*, vol. 27 (1982), beginning at page 345. Process conditions, recited at page 360, do not require the use of a solvent, although an organic amine can apparently function as a solvent. Other solvents used heretofore include acetonitrile, methanol, dimethylformamide, N-methylpyrrolidinone and hexamethyl phosphoramide.

Heck, U.S. Pat. No. 3,922,299, incorporated herein by reference, teaches that the reaction can be carried out with or without a solvent. Suggested solvents include acetonitrile, tetrahydrofuran or excess olefin.

The Heck vinylation reaction has been used to vinylate various kinds of compounds, including vinylation using vinylically-unsaturated organosilicon compounds. The preparation of polysiloxane-bridged bisbenzocyclobutene monomers has been recited by Gros, U.S. Pat. No. 4,759,874, and Schrock, U.S. Pat. No. 4,812,588, both herein incorporated by reference. Other silane-containing compounds have been synthesized by Hahn et al., U.S. Pat. No. 4,831,172, herein incorporated by reference. Similar synthesis of benzocyclobutene compounds is disclosed by Kirchhoff, U.S. Pat. No. 4,540,763, herein incorporated by reference.

Known processes for reaction between halogenated organic compounds and hydrolytically-stable, vinylically-unsaturated precursor compounds have been carried out in organic solvents.

It has surprisingly been found that the Heck-type vinylation reaction can be carried out in aqueous media, including aqueous solutions of organic solvents.

It is therefore the object of this invention to provide an improved process for vinylation of halogenated organic compounds, wherein an aqueous diluent is used.

DISCLOSURE OF INVENTION

This invention relates to a process for preparing a vinylically-unsaturated product compound, comprising reacting a halogenated organic compound with a hydrolytically-stable vinylically-unsaturated precursor compound in the presence of (a) a homogeneous zerovalent palladium catalyst complex, (b) an organic hydrogen halide acceptor and (c) a diluent, wherein the diluent is water or an aqueous solution containing up to 95% by volume of an organic solvent.

DETAILED DESCRIPTION OF THE INVENTION

The reaction between halogenated organic compounds and hydrolytically-stable, vinylically-unsaturated precursor compounds is carried out in the presence of a zerovalent palladium catalyst complex. The catalyst complex can be added to the reaction mixture or can be formed in the reaction mixture. Representative preformed catalyst complexes include tetrakis(triphenylphosphine)palladium (0), tris(dibenzylideneacetone)dipalladium (0) with triphenylphosphine and dichloro(triphenylphosphine)palladium (II).

The catalyst complex can be prepared in the reaction mixture, generally by reaction between a palladium (II) compound and a trivalent organophosphorus or organoarsenic compound.

The reaction between the vinylically-unsaturated precursor compound and halogenated organic compound, in the presence of a representative palladium complex, can be represented by the general equation:

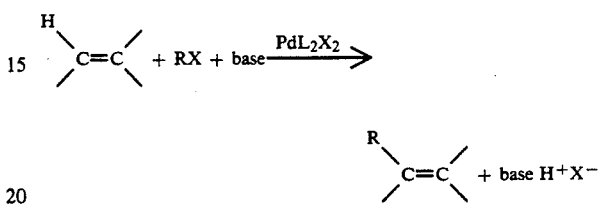

wherein R is aryl, heterocyclic, vinylic or benzyl and X is bromo, iodo or, rarely, chloro. L represents a ligand, which is a trivalent organophosphorus or organoarsenic compound. The base in the equation corresponds to the organic hydrogen halide acceptor.

Representative ligands in the Pd catalytic complex include, but are not limited to, triphenylarsine, triphenyl arsenite, tri-(n-butyl)phosphine, diphenylmethylphosphine, diphenylmethoxyphosphine, trimethyl phosphite, triphenylphosphine, triethylphosphine, phenyldi-(n-butoxy)phosphine, tris(p-anisyl)phosphine, tris-(o-tolyl)phosphine and tris-(o-tolyl) phosphite.

Palladium is introduced into the reaction mixture in the form of a salt, such as the acetate or chloride. It is postulated that the catalyst complex should contain two phosphine or arsine ligands per palladium atom.

Catalysts, or catalytic complexes, formed from palladium (II) acylates, particularly Pd(II) acetate, and triaryl phosphines have been found to be particularly preferred for the practice of this invention. Particularly preferred triaryl phosphines are triphenylphosphine and tris-(o-tolyl)phosphine.

Most preferred catalysts are those obtained from Pd (II) acetate and tris-(o-tolyl)phosphine.

The ratio of palladium (II) compound to phosphorus or arsenic ligand can be varied from about 1:1 to about 1:100. It is preferred to operate at ratios of from about 1:2 to about 1:10, particularly when a catalyst from Pd (II) acetate and tris-(o-tolyl)phosphine is used.

The amount of catalyst complex is varied from about 0.1 mol to 0.00001 mol (as Pd) per mol of halogenated organic compound in the reaction mixture. Preferably, the catalyst level is 0.01–0.00001 mol (as Pd) per mol of halogenated organic compound.

The organic hydrogen halide acceptor, used in the practice of this invention, is a secondary or tertiary amine. Representative organic hydrogen halide acceptors include, but are not limited to, trimethylamine, triethylamine, methylethylamine, diethyl-n-butylamine, triisobutylamine, tri-n-butylamine, diisopropylamine, triisopropylamine, N,N,N',N'-tetramethylethylene diamine, N-methylcyclohexylamine, N,N-diethylcyclohexylamine, N,N-diethylaniline, N,N-dimethylaniline, N-methyltoluidine, pyridine, quinoline, the lutidines, N-methylpiperidine, N-methylpyrrole and the like.

Preferred organic hydrogen halide acceptors are tertiary amines, particularly those represented by the formula $R_1R_2R_3N$, wherein each of $R_1$, $R_2$ and $R_3$ is selected independently from straight-chain and branched-chain alkyl of 1-8 carbon atoms and cycloalkyl. Most preferably, the organic hydrogen halide acceptor is triethylamine.

The molar ratio of organic hydrogen halide acceptor to halogenated organic compound can be varied from about 1:1 to about 10:1. Using greater excesses of organic hydrogen halide acceptor is not particularly advantageous. It has been found that excellent results are obtained using a 1-2 mols of organic hydrogen halide acceptor per mol of halogenated organic compound. Therefore, preferred ratios of organic hydrogen halide acceptor to halogenated organic compound are from about 1:1 to about 2:1.

The diluent can be water or an aqueous solution, containing up to 95% by volume of an organic solvent. When water is used as the diluent, the amount of water preferably exceeds 50% by weight of the combined organic reactants and organic hydrogen halide acceptor. Combined organic reactants means the combined weights of halogenated organic compound and hydrolytically-stable, vinylically-unsaturated precursor compound. More preferably, the amount of water exceeds 100% by weight of the combined organic reactants and organic hydrogen chloride acceptor. Preferably, the amount of water is less than 500% by weight of the combined organic reactants and organic hydrogen halide acceptor. The amount of water is selected, within these limits, so as to be sufficient to dissolve the hydrohalide salt, formed during the reaction. Use of an amount of water, sufficient to dissolve salts formed by the reaction, greatly facilitates isolation and purification of the reaction products.

The use of an aqueous solvent in the process does not adversely affect the yield or product distribution. Use of a diluent, containing significant amounts of water prevents formation of intractable salt accumulations in the reactor and on the stirrer. A reaction medium, from which by-products do not accumulate on the walls of the reactor or stirrer, provides for more efficient heat transfer and for better agitation than possible when salt-cake formation occurs.

In some cases, phase separation into an aqueous salt-containing layer and an organic product-containing layer occurs. Separation of the reaction mixture into a two-phase system is very desirable and facilitates removal of the by-product salt and isolating the desired product from the organic phase.

Aqueous solutions of organic solvents, also used a diluents, preferably contain up to 90% by volume of organic solvent. Organic solvents can be selected from nitriles, alcohols, ketones, linear or cyclic saturated esters, N,N-dialkylformamides, N-alkylpyrrolidinones, alkoxyalkanols, glycol ethers, dioxane, tetrahydrofuran, tetrahydropyran or hexaalkylphosphoramides.

Suitable nitriles include, but are not limited to, acetonitrile, propionitrile, butyronitrile, and higher aliphatic nitriles, as well as benzonitrile, tolylnitrile, methoxybenzonitrile, etc. A preferred nitrile solvent is acetonitrile.

Alcohols which can be used in the aqueous diluent solutions include alkanols of 1-8 carbon atoms, including the various isomeric forms.

Esters useful in aqueous diluent solutions include linear or cyclic saturated esters, for example, ethyl acetate, methyl propionate, isopropyl butyrate, caprolactone and butyrolactone.

Ketones, useful in the aqueous diluent solutions, include acetone, methyl ethyl ketone, methyl isopropyl ketone, and similar compounds.

Of the various N,N-dialkylformamides which can be used in the aqueous diluent, N,N-dimethylformamide is most preferred.

N-Methylpyrrolidinone is preferred among the various N-alkylpyrrolidinones.

Alkoxyalkanols suitable for use in aqueous diluents include those of up to about 10 carbon atoms, e.g. ethylene glycol monomethyl ether, propylene glycol monoethyl ether, ethylene glycol monobutyl ether, propylene glycol monoisopropyl ether, etc.

Glycol ethers, including ethylene glycol dimethyl or diethyl ethers, corresponding propylene glycol ethers, or diethylene glycol or triethylene glycol diethers can also be used.

Of the hexaalkylphosphoramides which can be used in the aqeuous diluents, hexamethylphosphoramide is preferred.

Preferred aqeuous diluents are those containing 10-90% by volume of N,N-dimethylformamide or N-methylpyrrolidinone. Most preferred diluents are aqueous solutions containing 30-70% by volume of dimethylformamide or N-methylpyrrolidinone.

Most preferably, the process of this invention is one wherein the diluent is an aqueous solution of 30-70% by volume of N,N-dimethylformamide or N-methylpyrrolidinone and the diluent is present in an amount equal to at least 70% by weight of combined halogenated organic compound, hydrolytically-stable, vinylically-unsaturated precursor compound and organic hydrogen halide acceptor.

Halogenated organic compounds, useful as starting materials for the process of this invention, include mono- and polycyclic, substituted or unsubstituted carbocyclic or heterocyclic aromatic bromo and iodo compounds and, rarely, chloro compounds, provided that any substituent is inert under the reaction conditions employed. Aryl iodides may react in the presence of Pd (0), without a phosphine or arsine ligand. The reactive halogenated organic compounds can be classified broadly as aryl halides, benzyl halides or vinylic organic halides.

Benzyl halides include substituted and unsubstituted benzyl chlorides, bromides and iodides. The benzyl chlorides are sufficiently reactive to add to a vinylically-unsaturated precursor compound. Benzyl chlorides and halides are preferred reagents for this synthesis. Substituents on the aromatic ring of the starting benzyl halide include straight and branched chain alkyl, alkoxy, nitro, cyano, hydroxy, keto, amide, carboxy, dialkylamino and sulfone groups. It will be understood that 1-halobenzocyclobutenes represent a type of benzyl halide.

Vinylic halides, useful in the practice of this invention include, for example 1-and 2-iodoalkenes and 1-or 2-bromoalkenes of the formulas $CH_2=CXR$ or $CHX=CHR$, wherein R is alkyl or aryl and X is I or Br.

Aromatic halides include substituted and unsubstituted aryl bromides and iodides. Aryl chlorides generally are unreative under the conditions used. Substituents on the aromatic ring or rings can include straight and branched chain alkyl, alkoxy, nitro, cyano, hydroxy, ketone, amide, carboxy, dialkylamino or sulfone groups. Aromatic halides include both monocyclic and polycyclic aromatic halides.

Representative heterocyclic reactants include, but are not limited to, bromofuran, bromopyridine, bromo-N-methylpyrrole, iodofuran, iodolutidine, etc.

Preferably, the halogenated organic compound used as feed is selected from bromo- or iodo- mono- or polycyclic substituted or unsubstituted carbocyclic or heterocyclic compounds or substituted or unsubstituted benzyl chlorides or bromides. Bromo compounds are most preferred as starting materials.

Substituents on substituted halogenated carbocyclic aromatic compounds are preferably selected from alkyl of 1-6 carbon atoms, alkoxy of 1-6 carbon atoms, chloro or cyano. It will be appreciated that alkyl and alkoxy substituents can be straight-chain or branched-chain.

A class of preferred reactants includes bromo- or iodo- benzocyclobutenes, as disclosed by Gros, U.S. Pat. No. 4,759,874, supra. Most preferably, the reactant is a brominated benzocyclobutene, represented by the formula

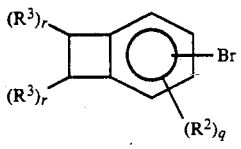

wherein $R^2$ is alkyl of 1-6 carbon atoms, acyloxy of 1-6 carbon atoms, alkoxy of 1-6 carbon atoms, nitro or chloro; each $R^3$ is independently alkyl of 1-6 carbon atoms, aryl, nitro, chloro or cyano; q is 0, 1, 2 or 3 and each r is independently 0 or 1.

Brominated benzocyclobutenes can be prepared as recited by Liu, U.S. Pat. No. 4,822,930, herein incorporated by reference. Most preferably, 4-bromobenzocyclobutene is used in processes of this invention. This starting material is obtained in high purity by distilling materials in accordance with Liu '930.

It will be understood that "benzocyclobutene" is an art-recognized term for a cyclobutarene compound, Liu '930. Cyclobutarene compounds are compounds, containing at least one aromatic ring, which is fused to one or more substituted or unsubstituted cyclobutene rings. An aromatic ring contains (4N+2)n electrons, as described in Morrison and Boyd, *Organic Chemistry*, third edition (1973). In the numbering system for benzocyclobutenes, the 1- and 2-positions are in the cyclobutene ring. The 3- and 6-positions are in an aromatic ring, adjacent to the cyclobutene ring. The 4- and 5-positions are meta- to the cyclobutene ring. Benzocyclobutenes are formally identified as derivatives of bicyclo[4.2.0]octa-1,3,5-triene. correlations between various representative names and structures are given in Table 1.

Preferred halogenated organic compounds include brominated and iodinated alkylbenzenes and alkylnaphthalenes or corresponding alkoxy compounds, wherein alkyl and alkoxy are of 1-6 carbon atoms and can be of any isomeric structure. A particularly preferred halogenated organic compound is of the formula ArBr, wherein Ar is substituted or unsubstituted monocyclic aromatic. Most preferred as a halogenated organic compound is that wherein Ar is phenyl or o-, m- or p-tolyl, or a mixture thereof. The use of o-alkylbromobenzenes, which react with various olefins to provide a feasible process for making hitherto hard-to-synthesize o-vinylalkylbenzenes, is particularly preferred.

Also preferred as halogenated organic compounds are substituted or unsubstituted benzyl chlorides or bromides, particularly those wherein the substituent is alkyl or alkoxy of 1-6 carbon atoms.

TABLE 1

Structures and Names of Representative Reactants and Products

| Short Name | Structure | Alternative Names |
|---|---|---|
| 4-BrBCB | Br—[structure] | 3-bromobicyclo[4.2.0]octa-1,3,5-triene<br>4-bromobenzocyclobutene |
| DVS | [H$_2$C=CHSi(CH$_3$)$_2$]$_2$O | 1,1'-divinyltetramethyldisiloxane<br>1,3-divinyltetramethyldisiloxane |
| BCB—VT | 4-BCBCH=CHC$_6$H$_4$CH$_3$ | [(4-benzocyclobutenyl)vinyl]toluene<br>3-[2-(methylphenyl)ethenyl]bicyclo[4.2.0]octa-1,3,5-triene |
| DVB—bis—BCB | (4-BCB—CH=CH)$_2$C$_6$H$_4$ | bis-[(4-benzocyclobutenyl)vinyl]benzene |
| DVB—BCB$_2$ | [(4-BCB—CH=CH)—Si(CH$_3$)$_2$]$_2$O | 1,1'-bis-[(4-benzocyclobutenyl)vinyl]tetramethyldisiloxane<br>1,3-bis-(2-bicyclo[4.2.0]octa-1,3,5-trien-3-yl-ethenyl)-1,1,3,3-tetramethyldisiloxane |
| vinyl-BCB | 4-BCB—CH=CH$_2$ | 4-vinylbenzocyclobutene<br>3-ethenyl-bicyclo[4.2.0]octa-1,3,5-triene |
| bis—BCB-ethylene | 4-BCB—CH=CH—BCB-4 | 1,2-bis(4-benzocyclobutenyl)ethylene<br>3,3'-(1,2-ethenediyl)bisbicyclo[4.2.0]octa-1,3,5-triene |
| DVS—BCB | 4-BCB—CH=CH—Si(CH$_3$)$_2$OSi(CH$_3$)$_2$CH=CH$_2$ | 1-[(4-benzocyclobutenyl)vinly]-1'-vinlytetramethyldisiloxane |

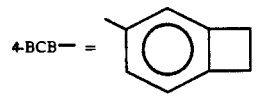

Vinylic iodides or bromides are also preferred.

Hydrolytically-stable, vinylically-unsaturated precursor compounds employed in the process of this invention can be selected from three general classes of compounds:

(a) a vinyl, allyl or methallyl organosilicon compound;

(b) hydrocarbon compounds, including vinyl, allyl and methallyl hydrocarbons, of various degrees of substitution; and (c) compounds containing vinyl, allyl or methallyl moieties and one or more of oxygen, nitrogen, phosphorus or sulfur atoms, or a combination thereof.

Organosilicon compounds are commercially available. A representative source is Petrarch Systems, Inc., Bartram Road, Bristol, Pa., 19007. See, for example, Petrarch's "Silicon Compounds Register and Review," (1987), page 114, which recites the availability of bis(-dimethylamino)methylvinylsilane, 1-bromovinyltrimethylsilane, tert.-butyldimethylvinylsilane, divinyldimethylsilane, 1,3-divinyl-1,3-diphenyl-1,3-dimethyldisiloxane, 1,3-divinyl-1,3-diphenyl-1,3-dimethyldisilazane, 1,3-divinyl-1,1,4,4-tetramethyldisilylethylene, phenyldimethylvinylsilane, phenylmethylvinylsilane, polyvinylmethylsiloxane, 1,1,3,3-tetravinyldimethyldisiloxane, tetravinylsilane, 1,3,5,7-tetramethylcyclotetrasiloxane, triphenylvinylsilane, tris(vinyldimethylsiloxy)methylsilane, tris(vinyldimethylsiloxy)methylsilane, trivinylmethylsilane and 1,3,5-trivinyl-1,1,3,5,5-pentamethyltrisiloxane, any of which is exemplary of hydrolytically-stable organosilicon compounds, useful in the practice of this invention. Preferred organosilicon compounds include those containing vinyl, allyl or methallyl function, bonded to silicon. Trialkylvinylsilanes, wherein alkyl is of 1-6 carbon atoms, are preferred.

A further group of preferred organosilicon compounds are di- and higher polysiloxanes, represented by the formula

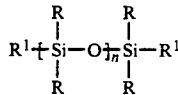

wherein each R is independently alkyl of 1-6 carbon atoms, cycloalkyl, aralkyl or aryl; each $R^1$ is independently vinyl, allyl or methallyl; and n is an integer from 1 to 4500.

Most preferably, $R^1$ is vinyl and each R is methyl, ethyl or phenyl. Preferred siloxanes are those wherein n is 2-10. Several of these compounds are available from Petrarch Systems, above. A most preferred member of this group of compounds is 1,1'-divinyltetramethyldisiloxane, represented by the formula $[CH_2=CHSi(CH_3)_2]_2O$.

Hydrocarbon hydrolytically-stable, vinylically-unsaturated precursor compounds useful in the process of this invention include compounds having a vinyl, allyl or methallyl function, whether substituted or unsubtituted by another hydrocarbon function. Compounds containing a plurality of vinyl, allyl or methallyl functions can be used, including those wherein the unsaturated bonds are conjugated. Representative hydrolytically-stable, vinylically-unsatured hydrocarbon compounds for the purposes of this invention include, but are not limited to, ethylene, propylene, 1-butene, 2-butene, 2-methyl-1-propene, 1,3-butadiene, 2-methyl-1,3-butadiene, 1,4-pentadiene, 1,5-hexadiene, 3-methyl-1-butene, styrene, substituted styrenes, divinylbenzenes, diallylbenzenes, di(methylallyl)benzenes, 1-and 2-vinylnaphthalene and substituted vinylnaphthalenes, vinylcyclohexane, stilbene, vinylcyclopentane, allylcyclohexane, methallylcyclohexane and substituted cyclopentanes and cyclohexanes. Substituents include alkyl and aryl groups, e.g., alkyl of 1-6 carbon atoms, phenyl, tolyl, xylyl, etc.

Preferred hydrolytically-stable, vinylically-unsaturated precursor compounds useful as starting materials for the process of this invention include ethylene, styrene, various vinyltoluene or divinylbenzene isomers, including mixtures of isomers.

It will be understood that the process of this invention contemplates stepwise reaction between several moles of halogenated organic compound per mole of hydrolytically-stable, vinylically-unsaturated precursor compound. For example, 4-bromobenzocyclobutene (4-BrBCB) can be reacted with ethylene to produce (4-benzocyclobutenyl)ethylene, 1,2-bis-(4-benzocyclobutenyl)ethylene and 1,1,2-tris-(4-benzocyclobutenyl)ethylene.

Intermediate reaction products, for example, stilbene, can be reacted with additional halogenated organic compounds. Stilbene can be reacted with 4-BrBCB to produce 1,2-diphenyl-1,2-bis-(4-benzocyclobutenyl)ethylene. Reacted with 2-bromotoluene, ethylene could produce o,o'-dimethylstilbene, etc.

Hydrolytically-stable vinylically-unsaturated precursor compounds include those containing as a hetero atom one or more of oxygen, nitrogen, phosphorus or sulfur, or a plurality thereof. These compounds include, but are not limited to acrylate and methacrylate esters, acrolein, methacrolein, ethacrolein, crotonaldehyde, vinyl acetate, vinyl octoate, vinyl propionate, vinyl versatate, vinyl laurate, allyl acetate, methallyl acetate, allyl versatate, methallyl laurate, allyl stearate, nitroethylene, nitropropylene, nitrostyrene, nitro-alpha-methylstyrene isomers, methyl vinyl ether, ethyl vinyl ether, stearyl vinyl ether, isostearyl vinyl ether, allyloxymethane, allyloxyethane, methallyloxypropane, phenyl vinyl ether, allyloxybenzene, acrylonitrile, methacrylonitrile, acrylamide, methacrylamide, N,N-diethylacrylamide, vinyl diethyl phosphite, divinylmethylphosphine, methyl vinyl thioether, etc, vinylphosphonic acid, allylphosphonic acid, etc.

Preferred hydrolytically-stable O, S, N or P compounds include acrylonitrile or methacrylonitrile and further include acrylate or methacrylate esters, wherein the alcohol moiety is alkyl of 1-30 carbon atoms or substituted or unsubstituted mono- or bicyclic aryl.

Most preferred products, obtained by the process of this invention, are those prepared from:
(a) 4-bromobenzocyclobutene and a mixture of m- and p-vinyltoluene;
(b) 4-bromobenzocyclobutene and 1,1'-divinyltetramethyldisiloxane;
(c) 4-bromobenzocyclobutene and divinylbenzene
(d) ethylene and o-bromotoluene
(e) 4-bromobenzocyclobutene and ethylene and
(f) 4-bromobenzocyclobutene and styrene.

The molar ratio of halogenated organic compound to hydrolytically-stable, vinylically-unsaturated precursor compound can be determined by routine experimentation. Generally, molar ratios of about 0.5:1 to 1.5:1 will be preferred for the synthesis of monoadducts. Higher molar ratios of halogenated organic compound to hydrolytically-stable, vinylically-unsaturated precursor will be employed when higher adducts are being prepared.

The temperature at which the process of this invention is performed can be from about room temperature to the temperature at which the starting materials or products decompose or polymerize. Elevated temperatures are normally preferred. It has been found that heating under reflux, generally at 80°-120° C., usually permits a reasonable reaction rate. The temperature conditions for a given set of reactants and diluent can readily be ascertained by routine experimentation.

For certain applications, the compounds prepared by the process of this invention are acceptable, without further purification. For example, reaction products from halogenated aromatic compounds and ethylenically-unsaturated hydrocarbons or compounds containing N, O, S or P can be used without purification more stringent than distillation or crystallization, as may be apparent to a person skilled in the art.

Products with extremely low ionic impurity levels are required when the products are being used, for example, as adhesion promoters for electronic devices. Adhesion promoters must be free of significant levels of phosphorus impurities. It has been found that treating a crude reaction mixture with a peroxide is effective to oxidize phosphine residues to a corresponding phosphine oxide.

Aqueous hydrogen peroxide can be used for this purpose. The crude product is treated with aqueous hydrogen peroxide at ambient or somewhat elevated temperatures for a time sufficient to oxidize residual phosphine to phosphine oxide.

Preferably, oxidation of phosphine residues is done using an organic peroxide. Preferred organic peroxides include hydroperoxides, peresters and peracids, of which tert-butyl hydroperoxide, cumene hydroperoxide, perbenzoic acid, m-chloroperbenzoic acid, monoperphthalic acid and peracetic acid are representative. tert-Butyl hydroperoxide is preferred. Treatment with an organic peroxide can be done at ambient temperature or at temperatures up to 80°-90° C.

It is preferred to purify the crude reaction products by chromatography over silica gel or alumina. This accomplishes removal of palladium residues and, when used after treatment of a crude product with a peroxide, also removes phosphine oxide.

When ultrapure, ionic-free, reaction products are required, as for adhesion promoters in electronic applications, it is preferred to treat crude reaction products with aqueous hydrogen peroxide or tert-butyl hydroperoxide and to chromatograph the crude products over silica or alumina. These purification steps can be carried out in either order.

The compounds prepared by the process of this invention have a variety of utilities. o-Vinyltoluene is an ethylenically-polymerizable monomer, useful for making resins. Derivatives of benzocyclobutenes polymerize thermally by formation of o-xylylene moities, which can undergo Diels-Alder condensation reactions with mono-enes and provide a route to polymers with high temperature stability. Benzocyclobutenes can also act as crosslinking agents in polymers, as disclosed by Wong (U.S. Pat. No. 4,622,375).

Accordingly, preferred processes of this invention are those wherein:

(a) the halogenated organic compound is a bromo or iodo mono- or polycyclic substituted or unsubstituted carbocyclic or heterocyclic compound or a substituted or unsubstituted benzyl chloride, bromide or iodide;

(b) the halogenated organic compound is a brominated benzocyclobutene represented by the formula

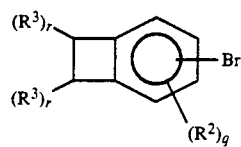

wherein $R^2$ is alkyl of 1-6 carbon atoms, alkoxy of 1-6 carbon atoms, trifluoroacetoxy, acyloxy of 1-6 carbon atoms, nitro or chloro; each $R^3$ is alkyl of 1-6 carbon atoms, aryl, nitro, chloro or cyano; q is 0, 1, 2 or 3 and each r is independently 0 or 1;

(c) the halogenated organic compound is 4-bromobenzocyclobutene;

(d) the halogenated organic compound is of the formula ArBr, wherein Ar is phenyl or o-, m- or p-tolyl;

(e) the halogenated organic compound is a substituted or unsubstituted benzyl bromide or chloride;

(f) the halogenated organic compound is a vinylic bromide;

(g) the hydrolytically-stable, vinylically-unsaturated precursor compound is a vinyl, allyl or methallyl organosilicon compound, including each of (a)-(f);

(h) the hydrolytically-stable, vinylically-unsaturated precursor compound is a trialkylvinylsilane, wherein alkyl is of 1-6 carbon atoms, including each of (a)-(f);

(i) the hydrolytically-stable, vinylically-unsaturated precursor compound is of the formula

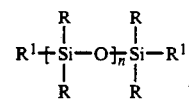

wherein each R is independently alkyl of 1-6 carbon atoms, cycloalkyl, aralkyl or phenyl; each $R^1$ is independently vinyl, allyl or methallyl and n is an integer from 1 to 4500, including each of (a)-(f);

(j) the hydrolytically-stable, vinylically-unsaturated precursor compound is

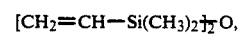

including each of (a)-(f);

(k) the hydrolytically-stable, vinylically-unsaturated precursor compound is a hydrocarbon, including each of (a)-(f);

(l) the hydrolytically-stable, vinylically-unsaturated precursor compound is ethylene, including each of (a)-(f);

(m) the hydrolytically-stable, vinylically-unsaturated precursor compound is styrene, including each of (a)-(f);

(n) the hydrolytically-stable, vinylically-unsaturated precursor compound is o-, m- or p-vinyltoluene or a mixture thereof, including each of (a)-(f);

(o) the hydrolytically-stable, vinylically-unsaturated precursor compound is o-, m- or p-divinylbenzene or a mixture thereof, including each of (a)-(f);

(p) the hydrolytically-stable, vinylically-unsaturated precursor compound contains one or more of an oxygen atom, a nitrogen atom, a sulfur atom or a phosphorus atom or a combination thereof, including each of (a)-(f);

(q) the hydrolytically-stable, vinylically-unsaturated compound is acrylonitrile or methacrylonitrile, including each of (a)-(f);

(r) the hydrolytically-stable, vinylically-unsaturated precursor compound is an acrylate or methacrylate ester, wherein the alcohol moiety is alkyl of 1-30 carbon atoms or substituted or unsubstituted mono- or bicyclic aryl, including each of (a)-(f);.

(s) the vinylically-unsaturated product compound is a reaction product of 4-bromobenzocyclobutene and a mixture of m- and p-vinyltoluene;

(t) the vinylically-unsaturated product compound is a reaction product of 4-bromobenzocyclobutene and 1,1'-divinyl-tetramethyldisiloxane;

(u) the vinylically-unsaturated product compound is a reaction product of 4-bromobenzocyclobutene and divinylbenzene;

(v) the vinylically-unsaturated product compound is a reaction product of ethylene and o-bromotoluene;

(w) the vinylically-unsaturated product compound is a reaction product of ethylene and 4-bromobenzocyclobutene;

(x) the vinylically-unsaturated product compound is a reaction product of styrene and 4-bromobenzocyclobutene;

(y) the catalyst is formed from palladium (II) acetate and a triaryl phosphine, including each of (a)-(x);

(z) the catalyst is formed from a palladium (0) complex and a triarylphosphine, including each of (a)-(x);

(aa) the catalyst is formed from palladium (II) acetate and tris-(o-tolyl)phosphine, including each of (a)-(x);

(bb) the organic hydrogen halide acceptor is a secondary or tertiary amine, including each of (a)-(aa);

(cc) the organic hydrogen halide acceptor is represented by the formula $R_1R_2R_3N$ and each of $R_1$, $R_2$ and $R_3$ is selected independently from straight-chain and branched-chain alkyl of 1-8 carbon atoms and cycloalkyl, including each of (a)-(aa);

(dd) the organic hydrogen halide acceptor is triethylamine, including each of (a)-(aa);

(ee) wherein the diluent is water, including each of (a)-(dd);

(ff) the diluent is water and is present in amount exceeding 100% by weight of combined halogenated organic compound, hydrolytically-stable, vinylically-unsaturated precursor compound and organic hydrogen halide acceptor, including each of (a)-(dd);

(gg) the diluent is an aqueous solution of up to 90% by volume of an organic solvent selected from the group consisting of nitriles, alcohols, linear or cyclic saturated esters, N,N-dialkylformamides, N-alkylpyrrolidinones, alkoxyalkanols, glycol ethers, ketones, dioxane, tetrahydrofuran, tetrahydropyran or hexaalkylphosphoramides, including each of (a)-(dd);

(hh) the diluent is an aqueous solution of 10-90% by volume of N,N-dimethylformamide, including each of (a)-(dd);

(ii) the diluent is an aqueous solution of 30-70% by volume of N-methylpyrrolidinone, including each of (a)-(dd);

(jj) the diluent is an aqueous solution of 30-70% by volume of N,N-dimethylformamide or N-methylpyrrolidinone and the diluent is present in an amount equal to at least 70% by weight of combined halogenated organic compound, hydrolytically-stable, vinylically-unsaturated precursor compound and organic hydrogen halide acceptor, including each of (a)-(dd);

(kk) a further step of treating a resulting crude product with a peroxide is included, including each of (a)-(jj);

(ll) a further step of chromatographing a resulting crude product over silica or alumina is included, including each of (a)-(kk); and (mm) the further steps of treating a resulting crude product with a peroxide and chromatographing the crude product over silica or alumina are included, including each of (a)-(jj).

BEST MODE FOR CARRYING OUT THE INVENTION

Most preferred products, prepared by the process of this invention are those prepared from:

(a) 4-bromobenzocyclobutene and a mixture of m- and p-vinyltoluene, (b) 4-bromobenzocyclobutene and 1,1'-divinyltetramethyldisiloxane, (c) 4-bromobenzocyclobutene and divinylbenzene (d) ethylene and o-bromotoluene (e) ethylene and 4-bromobenzocyclobutane and (f) styrene and 4-bromobenzocyclobutane.

A most preferred catalyst is that formed from palladium (II) acetate and tris-(o-tolyl)phosphine.

A most preferred diluent is aqueous dimethylformamide, containing 30-70% by volume of N,N-dimethylformamide.

Most preferably, a resulting crude product is treated with aqueous hydrogen peroxide or with tert-butyl hydroperoxide.

SPECIFIC EMBODIMENTS

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by weight.

EXAMPLE 1

Coupling of 4-Bromobenzocyclobutene with Mixed Isomers of Vinyltoluene in Aqueous Dimethylformamide The following materials are charged to a 5-L round-bottom flask, fitted out with a reflux condenser and magnetic stirring bar:

| | |
|---|---|
| 800 g | 4-bromobenzocyclobutene (4-BrBCB, 3-bromobicyclo[4.2.0]octa-1,3,5-triene) |
| 516 g | vinyltoluene (m/p = 70/30) |
| 968 g | triethylamine (Fisher, reagent grade) |
| 1000 mL | N,N-dimethylformamide (DMF, Fisher, certified A.C.S.) |
| 500 mL | deionized water |
| 0.976 g | palladium (II) acetate (Engelhard) |
| 5.344 g | tris-(o-tolyl)phosphine (Strem Chemicals, Inc.) |

The resulting two phase liquid mixture is purged with nitrogen and then stirred and heated under reflux (about 90° C.) under a stream of nitrogen. The reaction mixture remains essentially clear until all of the 4-BrBCB is reacted. At this point, a dark precipitate, which concentrates in the upper layer, is formed. The reaction is complete in 12-16 h.

At the end of the reaction, the mixture is cooled to room temperature and the clear bottom layer is removed by decantation in a separatory funnel. About 1500 mL of toluene is added to the upper layer and about 1000 mL of deionized water is added. The mixture is shaken and the lower aqueous layer is removed by decantation, as before. The toluene layer is extracted with 1000 mL of fresh deionized water.

The resulting toluene solution is split into two portions. Each half is passed through a column (3.175 cm inner diameter×66.04 cm high) packed with alumina (Fisher 80-200 mesh, basic alumina, Brockman Activity 1) to remove particulates. The columns are prepared by prepacking columns with 500 g of alumina, in the form of a slurry in toluene. After loading the column, the column is eluted with toluene. The effluent is a clear golden yellow solution, which is assayed for residual tris-(o-tolyl)phosphine (as phosphorus) by neutron activation analysis. Tri-(o-tolyl)phosphine is removed by stirring the toluene solution overnight with 250 mL of deionized water and 20 mL of 30% hydrogen peroxide at room temperature.

The lower toluene layer of the resulting two-phase solution is assayed by gas chromatography (Hewlett-Packard 5710 GC with a 3390 integrator using a J & W 30-meter narrow-bore capillary column, bonded with DB-1, 1.00 micrometer film thickness) for the presence of unreacted tris-(o-tolyl)phosphine. The temperature program is: isothermal at 100° C./2 min, ramp at 8° C./min to 230° C., hold at 230° C. for 8 or more minutes.

After all of the residual triarylphosphine has been converted to the phosphine oxide, the toluene solution is passed through a column packed with alumina, as above, to remove additional particulate matter and phosphine oxide. The effluent from the column is reduced in volume by removing toluene using a rotating evaporator. The product crystallizes after about 2 days at room temperature.

The isolated yield is 812 g (85% of theory).

The product is identical to a known sample, compared by gas chromatography, GC/MS and proton NMR.

The product contains less than: 0.5 ppm Pd, 5 ppm P (not detectable by gas chromatography), 1 ppm Cl, 0.5 ppm Br, or 1 ppm Na by x-ray fluorescence or neutron activation analyses.

EXAMPLE 2

Coupling of 4-Bromobenzocyclobutene with 1,1'-Divinyltetramethyldisiloxane in Aqueous Dimethylformamide The following reagents are changed to a 100-mL round-bottom flask, fitted out with a reflux condenser and magnetic stirring bar:

| | |
|---|---|
| 10 g | 4-bromobenzocyclobutene (4-BrBCB) |
| 5.08 | 1,1'-divinyltetramethyldisiloxane (Dow Corning) |
| 11.05 g | triethylamine (Fisher, reagent grade) |
| 25 mL | N,N-dimethylformamide (DMF, Fisher, certified A.C.S. grade) |
| 12.5 mL | deionized water |
| 0.026 g | palladium (II) acetate (Engelhard) |
| 0.146 g | tris-(o-tolyl)phosphine (Strem Chemicals, Inc.) |

The resulting two-phase liquid mixture is purged with nitrogen and stirred and heated under reflux (about 90° C.) under a stream of nitrogen. The upper layer remains clear until all of the BrBCB has reacted. At this point, a dark precipitate, which is concentrated in the upper layer, is formed. The reaction is complete, as indicated by metal deposition, after 12-16 h.

The crude reaction mixture is cooled, poured into 150 mL of deionized water and extracted with two 40-mL portions of pure n-heptane to extract the product. The combined heptane extracts are washed with three 150-mL portions of deionized water.

The crude product is analyzed by GC using a Hewlett-Packard 5890A gas chromatograph, fitted with a HP 7671A auto-sampler and HP 3392A integrator, using a J & W 15-meter wide-bore capillary column bonded with DB-5, 0.10 micrometer film thickness. The temperature program is to heat at 50° C. or 70° C. for 2 min, increase the temperature at a rate of 8°/min to 230° C. and hold at 230° C. for 8 or more min.

LC analysis is done using a reversed phase high pressure liquid chromatography (HPLC) technique for separating starting materials and products on a large pore (300 Å) Vydac C-10 column (46 mm×250 mm), using acetonitrile/water as eluants. The system is operated at ambient temperature with a flow rate of 1.5 mL/min. The eluate is analysed in the UV at 254 nm. The product contains no 4-BrBCB or divinyltetramethyldisiloxane.

The product-containing heptane extract is charged to a 100-mL round-bottom flask with 15 mL of methanol and 10 mL of 30% hydrogen peroxide solution and stirred overnight. The resulting solution is filtered through a 0.5 micron membrane filter and rinsed with two 150-mL portions of deionized water. A white solid, which precipitates and which is removed by filtration, is identified as a bisbenzocyclobutene adduct of ethylene, in an amount of about 0.2 g.

Heptane is removed from the resulting clear solution by evaporation using a rotary evaporator to produce 8.6 g of crude yellow product (40% of theory).

The crude product is diluted with 15 mL of n-heptane and passed through a column (1.91 cm inner diameter, 22.85 cm in length), packed with 25 g of J. T. Baker chromatography grade silica gel (60-230 Å). The material on the column is eluted with 100 mL of heptane to give 7.0 g of product. A dark band remains at about 3.81 cm from the top of the column and a light yellow band about 12.7 cm from the top of the column. Product is obtained by removing heptane from the main product fraction using a rotary evaporator and distilling the residue in a wiped film still.

The resulting product contains: less than 5 ppm Pd, less than 5 ppm P, about 4 ppm Cl, less than 1 ppm Br and less than 1 ppm Na by x-ray fluorescence or neutron activation analyses.

EXAMPLE 3

Coupling of 4-Bromobenzocyclobutene with Mixed Isomers of Vinyltoluene in Water

To a 100-mL round-bottom flask, fitted out with a reflux condenser and magnetic stirring bar, is charged:

| | |
|---|---|
| 10 g | 4-bromobenzocyclobutene |
| 6.44 g | vinyltoluene (m/p = 70/30, Dow Chemical Co.) |
| 11 g | triethylamine (Fisher, reagent grade) |
| 37.5 mL | deionized water |
| 0.0122 g | palladium (II) acetate (Engelhard) |
| 0.0664 g | tris-(o-tolyl)phosphine (Strem Chemical Co.) |

The resulting two-phase liquid mixture is purged with nitrogen and stirred and heated under reflux (about 90° C.). The reaction mixture turns black at the end of the reaction. At the end of 24 h, the upper layer contains all the reactants and the lower layer contains no organic materials, detectable by capillary GC (Hewlett-Packard 5710GC, as above). These analytical data are consistent with complete reaction of 4-BrBCB.

At the end of 24 h, the reaction mixture is cooled to room temperature and diluted with 25 mL of toluene. The resulting mixture is transferred to a 250-mL separatory funnel. The bottom aqueous layer is removed and the upper organic layer is diluted with 25 mL of toluene. The resulting organic layer is washed with four 100-mL portions of deionized water and filtered through magnesium sulfate to remove residual water and palladium.

The organic filtrate is charged to a 100-mL round bottom flask and stirred with 10 mL of 30% hydrogen peroxide for 4 h at room temperature. The layers are separated and the crude organic layer is washed with three 100-mL portions of distilled water and filtered through magnesium sulfate. The filtrate is passed over a column (1.91 cm inner diameter, 19.05 cm in length), packed with basic alumina (about 15 g, Fisher 80–200 mesh, basic alulmina, Brockman Activity 1). Toluene is removed from the column effluent using a rotary evaporator. The liquid product contains m/p-[(4-benzocyclobutenyl)vinyl] toluene (GC, as above) which crystallizes after standing overnight at room temperature to give 11 g of product (92% of theory).

The product contains: less than 1 ppm Pd, about 4 ppm P, about 2 ppm Cl, about 1 ppm Br and less than 1 ppm Na by x-ray fluorescence or neutron activation analyses.

EXAMPLE 4

Coupling of 4-Bromobenzocyclobutene with 1,1'-Divinylbenzene in Aqueous Solvent

The following reactants are charged to a 100-mL round bottom flask, fitted out with a reflux condenser and a magnetic stirring bar:

| | |
|---|---|
| 10 g | 4-bromobenzocyclobutene (Dow) |
| 3.64 g | divinylbenzene (95% - m/p 2/1, Dow) |
| 11 g | triethylamine (Fisher, reagent grade) |
| 37.5 g | deionized water |
| 0.0122 g | palladium (II) acetate (Engelhard) |
| 0.0664 | tris-(o-tolyl)phosphine (Strem Chemical Co.) |

The resulting two-phase liquid system is purged with nitrogen and stirred and heated under reflux (about 90° C.). The reaction mixture turns black soon after the reflux temperature is reached. After 24 hours' heating, the mixture is cooled and each layer of the resulting mixture is analyzed by GC and LC (Hewlett-Packard 5710GC, as above, and HPLC, as above). Conversion to product, which is in the upper layer, is complete.

Some solid precipitates from the cooled mixture. Toluene (25 mL) is added to the mixture, which is heated and poured while hot into a 250-mL separatory funnel. The bottom aqueous layer is removed. The organic layer is diluted with 25 mL of toluene and 100 mL of water and washed with four 100-mL portions of water.

The washed organic layer is heated to dissolve some solids and passed through a membrane filter (0.5 micron) to remove residual palladium.

The filtered solution is concentrated using a rotary evaporator to produce 9.6 g (52% of theory) of crystalline divinylbenzene-bis-BCB, alternatively, bis-[(4-benzocyclobutenyl)vinyl]benzene.

Analyses: Reversed-phase HPLC, as above. M.p. 148°–152° C., (Fisher-Johns melting point apparatus).

EXAMPLE 5

Coupling of 4-Bromobenzocyclobutene with 1,1'-Divinyltetramethyldisiloxane in Aqueous Solvent To a 100-mL round-bottom flask fitted with reflux condenser and magnetic stirring bar is charged:

| | |
|---|---|
| 10 g | 4-bromobenzocyclobutene (Dow) |
| 5.08 g | 1,1'-divinyltetramethyldisiloxane (Dow Corning) |
| 11 g | triethylamine (Fisher, reagent grade) |
| 37.5 mL | deionized water |
| 0.026 g | palladium (II) acetate (Engelhard) |
| 0.146 g | tris-(o-tolyl)phosphine (Strem Chemical Co.) |

The two-phase reaction mixture is purged with nitrogen and stirred and heated under reflux. The reaction mixture turns black shortly after reflux temperature (about 90° C.) is reached. The reaction is continued for 28 h, at the end of which the upper layer contains both reactants and products, detectable by GC (Hewlett-Packard 5890 A GC, as above).

At the end of 28 h, the GC analysis shows that the conversion of BrBCB is incomplete. Stirring and heating under reflux is continued for a total of 117 h, after which the reaction mixture is cooled and poured into a 150-mL separatory funnel and diluted with 40 mL of n-heptane. The aqueous layer is removed and the organic layer is washed with four 75-mL portions of distilled water. The resulting light yellow organic layer is dried by being passed over a layer of magnesium sulfate on a medium glass fritted filter.

The resulting organic filtrate is transferred to a 100-mL round bottom flask and stirred for 20 h at room temperature with 15 mL of 30% hydrogen peroxide. The liquid layers are separated and the organic layer is transferred to a separatory funnel and washed with four 65-mL portions of distilled water. The washed organic layer is filtered through a layer of magnesium sulfate on a fritted glass filtration funnel. The filtrate is concentrated using a rotary evaporator to yield 9.3 g (44% of theory) of crude 1,1'-[(4-benzocyclobutenyl)vinyl]tetramethyldisiloxane, of which the major component is formally known as 1,3-bis(2-bicyclo[4.2.0]octa-1,3,5-trien-3-ylethenyl)-1,1,3,3-tetramethyldisiloxane.

The crude product is taken up in about 20 mL of n-heptane and passed through a column (1.905 cm inner diameter, 33.02 cm in length) column, packed with 40 g of J. T. Baker chromatography grade silica gel (60–230 Å). The material on the column is eluted with 600 mL of n-heptane to give 6.7 g of pure product (more than 90% of 1,1'-bis-[(4-benzocyclobutenyl)vinyl]tetramethyldisiloxane isomers) after removing n-heptane on a rotary evaporator. An additional 1.5 g of yellow product was eluted from the column with acetone. This is lower purity product.

EXAMPLE 6

Coupling of 4-Bromobenzocyclobutene with Vinyltoluene in Aqueous Solution

The following reactants are charged to a 100-mL round-bottom flask, fitted out with a reflux condenser and magnetic stirring bar:

| | |
|---|---|
| 10 g | 4-bromobenzocyclobutene (0.054 mol, Dow) |

| 6.44 g | vinyltoluene (m/p = 70/30, 0.054 mol, Dow) |
| 5.51 g | triethylamine (0.054 mol, Fisher, reagent grade) |
| 37.5 mL | deionized water |
| 0.0122 g | palladium (II) acetate (Engelhard) |
| 0.0664 g | tris-(o-tolyl)phosphine (Strem Chemical Co.) |

The reaction is carried out as in Example 1. At the end of 22 h, the reaction mixture is analyzed by GC and contains about 5% of unreacted BrBCB and vinyltoluene and a trace of triethylamine. The major product is vinyltoluene adducts of BCB, systematically named 3-[2-(3- or 4-methylphenyl)ethenyl]bicyclo[4.2.0]octa-1,3,5-triene.

The product forms a glob in the reactor and is difficult to stir.

This example shows that using an excess of triethylamine acid acceptor is not required.

EXAMPLE 7

Reaction of Ethylene with Bromobenzocyclobutene (a) Reaction at 50° C.; Aqueous DMF; Triethylamine To a 300-mL Fluitron pressure reactor is charged 0.061 g of palladium acetate, 0.322 g of tris-(o-toly)phosphine, 50 g of 4-bromobenzocyclobutene, 55.2 g of triethylamine, 50 mL of N,N-dimethylformamide and 25 mL of water. The reactor is closed, purged with ethylene three times and filled and maintained with ethylene at 5.10 atm, gauge. The contents of the reactor are heated to 50° C. A sample after 20 hours' heating shows incomplete conversion (GC). Heating is continued until BCB conversion is nearly complete (140 h). The product contains 0.3% of BCB, 0.56% of BrBCB, 82.3% of 4-vinylbenzocyclobutene and 14.9% of 1,2-bis-(4-benzocyclobutenyl)ethylene.

(b) Reaction at 75° C.; Aqueous DMF; Triethylamine

To the 2-L reactor, described in Example 9, is charged 1.27 g of palladium acetate, 10 g of tris-(o-tolyl)phosphine, 500 g of bromobenzocyclobutene, 552 g of triethylamine, 1 g of MEHQ (hydroquinone monomethyl ether), 500 mL of N,N-dimethylformamide and 250 mL of deionized water. The reactor is closed and the reaction is run at 75° C. under 20.40 atm (gauge) of ethylene pressure. At the end of 24 hours' heating, a sample contained 86.68% of vinylbenzocyclobutene, 2.32% of bromobenzocyclobutene and 7.88% of 1,2-bis-(4-benzocyclobutenyl)ethylene.

The mixture is removed from the reactor. The organic phase is washed with water, neutralized with aqueous HCl and cooled to precipitate bis-adduct. The crude product weighs 359 g (theoretical 355 g). The product is distilled in vacuo.

(c) Triethylamine, DMF, Comparative Example

The reaction is run as in (b), using 500 g of 4-bromobenzocyclobutene, 552 g of triethylamine, 1.9 g of palladium (II) acetate, 1.0 g of tris-(o-tolyl)phosphine, 1.0 g of MEHQ and 750 mL of N,N-dimethylformamide instead of the aqueous mixture. The reaction mixture is heated to 85° C. under 20.40 atm (gauge) of ethylene. After 24 hours' heating, the reaction mixture contains 1.29% of bromobenzocyclobutene, 87.5% of vinylbenzocyclobutene and 5.87% of bis(benzocyclobutenyl)ethylene.

An accumulation of solids at the top of the reactor seals the top of the reactor to the body of the reactor. A screwdriver is required to pry the top of the reactor from the body. A donut-shaped salt cake lines the top and bottom of the reactor. The salt cake is chipped off and ground up. The salt cake is soluble in water. The salt cake appears to be mainly triethylamine hydrobromide.

The weight of crude product, worked up as above, is 304 g (86%).

(d) Triethylamine, DMF, Comparative Example

The reaction is run as in (c), the temperature being maintained at about 85° C. and ethylene pressure being maintained at about 6.80 atm (gauge). The solids content of the resulting mixture is very high. Addition of water to the mixture causes solids to float on the mixture.

(e) trans-1,2-Bis-(4-benzocyclobutenyl)ethylene

To a 2-L reactor, as in Example 9, is charged 0.28 g of palladium acetate, 1.50 g of tris-(o-tolyl)phosphine, 150 g of 4-bromobenzocyclobutene, 173 g of triethylamine, 350 mL of N,N-dimethylformamide and 175 mL of deionized water. The reactor is closed and purged three times with ethylene (5.10 atm, gauge) and maintained at this pressure. The reactor is heated and maintained at 72°-76° C.

After four hours' heating a sample contains 44.9% of vinylbenzocyclobutene and 52.4% of unreacted BrBCB. Ethylene is vented from the reactor and replaced with nitrogen (5.44 atm, gauge). Heating is continued. At the end of 49.5 hours' overall heating, a sample contains (GC) 90.0% of trans-1,2-bis-(4-benzocyclobutenyl)ethylene, 3.15% of vinylbenzocyclobutene and 3.0% of BrBCB.

The reactor is opened and the contents are poured into a 5-L round-bottom flask equipped with a stirring assembly and a bottom take-off. Deionized water (1.5 L) is added. The mixture is stirred and a resulting aqueous phase is separated and removed. Toluene (200 mL) is added to the mixture to dissolve precipitated solids and the organic layer is washed with two 1.5-L portions of deionized water. The organic phase is washed with 250 mL of 2N HCl in 1250 mL of deionized water to a final pH of about 3.

The organic layer is separated and passed through a layer of silica gel (5.08 cm), topped by a layer (1.27 cm) of magnesium sulfate, supported on a 1.0 micrometer membrane filter.

Toluene is removed from the filtrate under vacuum to leave 102 g of crude product (about 88% of theory) in the form of a slurry.

Product recrystallized from 100 mL of ethyl acetate gives 83.0 g of trans-1,2-bis-(4-benzocyclobutenyl)ethylene, m.p. 132° C. GC analysis detects one peak (99.7 area %).

(f) 1,1,2-Tris-(4-benzocyclobutenyl)ethylene

To a 100-mL one-necked flask equipped with a polytetrafluoroethylene-coated magnetic stirring bar and thermometer well are charged 12.5 mL of deionized water, 5.73 g (0.0568 mol) of triethylamine, 0.012 g (0.000026 mol) of palladium (II) acetate, 0.062 g (0.000103 mol) of tris-(o-tolyl)phosphine, 6.00 g (0.0258 mol) of trans-1,2-bis-(4-benzocyclobutenyl)ethylene and 25 mL of N,N-dimethylformamide.

The resulting solution is purged with a stream of nitrogen for 30 min, after which the solution is heated to 90° C. The reaction mixture is heated and stirred at 90° C. for 115 h. Gas chromatographic analysis of the crude reaction mixture indicates the mixture contains 0.5% of bromobenzocyclobutene, 0.4% of trans-1,2-bis-(4-benzocyclobutenyl)ethylene and 88.0% of 1,1,2-tris-(4-benzocyclobutenyl)ethylene.

The reaction mixture is allowed to cool to 80° C. and diluted with 40 mL of toluene. The organic layer is washed with 50 mL portions of 0.1N HCl until the aqueous layer remains acidic. The organic layer is washed with two 50-mL portions of deionized water and dried over magnesium sulfate. The solvent is removed in vacuo to give 8.3 g of a yellow oil.

The oil is dissolved in heptane and cooled to 5° C. The resulting crystals are separated by filtration to give 5.6 g of 1,1,2-tris-(4-benzocyclobutenyl)ethylene, m.p. 87°–89° C.

$^1$H NMR (CDCl$_3$): δ 6.6–7.3 (m, 10H), 2.9–3.3 (d, 12H); $^{13}$C[$^1$H] NMR (CD$_2$Cl$_2$, 75.1 MHz) 146.74, 146.31, 145.97, 145.82, 145.56, 145.09, 144.16, 144.00, 140,47, 137.33, 129.59, 129.50, 128.76, 127.22, 124.98, 123,81, 123.21, 122.67, 122.62, 122.39, 29.80, 29.59.

EXAMPLE 8

Coupling of Bromobenzene with Ethyl Acrylate (a) Aqueous DMF, Triethylamine

To a 100-mL one-necked flask, fitted out with a polytetrafluoroethylenecovered magnetic stirring bar, reflux condenser and thermometer well, is charged 8.57 g (0.0546 mol) of bromobenzene, 5.46 g (0.0546 mol) of ethyl acrylate, 11.02 g (0.1092 mol) of triethylamine, 0.0246 g (0.00011 mol) of palladium (II) acetate, 0.134 g (0.00044 mol) of tris-(o-tolyl)phosphine, 25 mL of N,N-dimethylformamide and 12.5 mL of deionized water. The atmosphere over the solution is purged with nitrogen and a nitrogen pad is maintained over the mixture during the reaction. The reaction mixture is heated to 90° C. for 16 h. Gas chromatographic analysis of the mixture shows that the reaction mixture contains 94.7% of ethyl 3-phenylpropenoate.

$^1$NMR (CDCl$_3$): δ 7.6 (d, 1H, J=32 Hz); 6.4–7.4 (m, 5H), 6.3 (d, 1H, J=32 Hz), 4.2 (q, 2H, J=14 Hz), 1.3 (t, 3H, J=14 Hz).

EXAMPLE 9

Coupling of Bromotoluene with Ethylene

Reactions are run in a stainless steel 2-L Parr reactor, equipped with an air-motor-driven stirring shaft, gas inlet tube equipped for purging with nitrogen and ethylene, pressure gauge, sampling system, internal thermowell, frangible blow-out member and a vent. Heating is provided by an electrically-heated mantle, connected to a high-limit shutoff and a West temperature controller, attached to a Molytek model 2702 recorder.

Samples are analyzed by GC using a Hewlett-Packard 5890 gas chromatograph with a flame ionization detector, a 7676A automatic sampler and a Hewlett-Packard 3390 integrator using known standards of pure o- or p-vinyltoluene (OVT, PVT). The column is 15 m×0.32 mm DB-5 (0.1 micrometer film) fused silica capillary. The injector temperature is 250° C.; the detector temperature is 300° C. The program is: maintain at 70° C./2 min; heat at 8° C./min ramp to 230° C. The flow rate for carrier gas is 1.7 atm (gauge), mu=38 cm/sec (isobutane at 200° C.). Flow rates are: hydrogen, 30 mL/min; air 400 mL/min, make-up, 30 mL/min (helium), split flow, 187 mL/min (helium). The septum purge rate is 0.56 mL/min. The sample size (automated) is 2 microL.

(a) Coupling in Aqueous DMF; o-Bromotoluene; Triethylamine

To the reactor is charged 374 g (2.187 mol) of 2-bromotoluene (98%, Aldrich), 442 g of triethylamine (reagent grade, Fisher), 0.59 g (0.0026 mol) of palladium (II) acetate (Engelhard), 3.18 g (0.0104 mol) of tris-(o-tolyl)phosphine (Strem Chemical Co.), 600 mL of N,N-dimethylformamide (Fisher) and 300 mL of deionized water. The reactor is sealed and attached to the reaction system. After stirring is initiated, the contents of the vessel are purged with nitrogen (5.44 atm, gauge) five times. The nitrogen is vented and the reactor is charged with ethylene (Scott Gas) to 5.10 atm, gauge and held at this pressure.

A sample of about 5 mL is removed from the double-valved sample dip tube and used for a gas chromatography trace of the initial feed sample. Additional samples are removed during the reaction by discarding the first several samples to rinse the dip tube before using a later sample for GC analysis.

The temperature controller is set at 75° C. and heating is initiated. The contents of the reactor reached the selected temperature after 30 min and is maintained at that temperature for the duration of a run.

A mixture of pure o-vinyltoluene and o-bromotoluene is analyzed on the GC. o-Vinyltoluene and o-bromotoluene have retention times of 0.89 min and 1.14 min, respectively. The contents of the reactor are sampled after 2, 4, 20.5, 28 and 45 h. The conversion of o-bromotoluene is incomplete after 45 h. The reactor is cooled to 30° C. and opened in a hood for the addition of 0.030 g of palladium acetate and 1.59 g of tris-(o-tolyl)phosphine. The vessel is resealed, reattached to the system, purged with nitrogen as before and repressurized with 5.10 atm (gauge) of ethylene. The contents of the reactor are heated to 75° C. At the end of 2 hours' further heating, the sample removed shows complete conversion. The contents of reactor are stirred and cooled to room temperature. The reactor is vented and the reaction vessel is opened.

The contents of the reactor are poured into a 5-L three-necked glass round-bottom flask containing 1 L of methylene chloride (Burdick & Jackson) and 1 L of deionized water. The flask has a bottom dump valve and is stirred by an air-driven stirrer. The contents of the flask are stirred for 5 min and the top aqueous phase is discarded. The organic phase is washed with two 1.5-L portions of deionized water; two 250mL portions of 5N HCl in 1250 mL of deionized water and two further 1.5-L portions of deionized water. The aqueous layer is discarded after each wash.

The organic phase is filtered through a short column prepared using a 300 mL Fisherbrand microfiltration system with a 5-micron membrane filter, containing 150 mL of silica gel (Fisher, chromatographic 644 grade, type 150A, 100–200 mesh), topped with a 1.90 cm layer of magnesium sulfate. Filtration accomplishes removal of residual solids and catalyst and dries the solution.

Methylene chloride is removed from the filtrate on a Buchi Rotavaporizer Model RE 120 at 40° C. at 15 mm Hg. The weight of crude reaction product is 227.6 g. The crude product is charged to a 500-mL round-bottom flask and attached to a 20.32-cm Bantamware column packed with glass helices, attached to a Bantamware one-piece distillation unit equipped with a vacuum-jacketed Vigreaux section and fraction cutter. The distillation setup is connected to a McCloud gauge, a nitrogen source, a dry ice (−78° C.) trap, high-vacuum pump, heating mantle, temperature controller and temperature high-limit cutoff. The crude product is degassed and methylene chloride is removed with stirring until bubbling stopped. The distillation pot is heated to 50° C. at about 0.4 mm Hg. The first fraction (about 20 g) is collected at 24°-25° C./0.35 mm Hg. The second fraction (114.7 g) is collected at a pot temperature up to 55° C. The first and second fractions are identified as 100% pure o-vinyltoluene (GC). The dry ice trap contains 31.6 g of o-vinyltoluene, containing a trace of methylene chloride. The pot residue (53.2 g) crystallizes upon cooling. The pot residue contains 3.5% of o-vinyltoluene (OVT), 60% of transdisubstituted product, 30% of 1,1 (gem)-disubstituted product and 4% of tris-(o-tolyl)phosphine.

The combined yield of OVT (134.7+31.6) is 166.3 g (64% of theory).

(b) Coupling in Aqueous DMF; Higher Catalyst Level; o-Bromotoluene; Triethylamine The reaction is as in (a), except that 0.98 g (0.00437 mol) of palladium (II) acetate and 5.32 g of tris-(o-tolyl)-phosphine are used as catalyst. The reactor is loaded as above and the temperature is increased to 120° C. Ethylene pressure is 13.6 atm, gauge. Samples are taken for analysis at 0, 3 and 5 h. At the end of 5 h, only a trace of bromotoluene is present (GC). The product contains 75.3% of OVT, 16% of trans-diadduct and 6.8% of gem-diadduct. The reactor is shut down after 7 hours' heating, as above.

The product is worked up as above to give 241 g of crude product. The mixture is purified by distillation at 8.0 mm Hg, at which product boiled at 50°-51° C. and no product was collected in the cold trap. The first cut gave 10 g of OVT (99%); the second cut gave 131 g of OVT (99.34%). A third cut (25.4 g 50°-51° C., 8 mm Hg) contains 98.6% of OVT and 1.2% of o-bromotoluene.

The pot residue (61.2 g) is mainly diadduct. The recovered OVT weights 166.4 g (64.4% of theory).

(c) Coupling of p-Bromotoluene and Ethylene, Aqueous DMF, Triethylamine

The reaction is run as in part (b), except that p-bromotoluene is used instead of o-bromotoluene. The reaction is run at 123° C., with cooling to 112° C. after an initial exotherm. Samples are taken at 0,3 and 5 h and used for GC analyses. At the end of three h, the GC shows 77.65% of p-vinyltoluene (PVT), less than 0.5% of p-bromotoluene, 18.1% of trans-diadduct and 3.0% of gem-diadduct. The reactor is cooled after 5 hours' heating, at which point GC indicates complete conversion of bromotoluene to 73.5% PVT, 20.9% of trans-diadduct and 3.4% of gem-diadduct.

The product is worked up as in (b), except that 1.5 L of additional methylene chloride is used to dissolve precipitated solids. The solids are isolated, purified and characterized as trans-p-methylstilbene dicoupled product, m.p. 179° C. (51 g). The total yield of isolated crude products is 225.5 g, comprising 72.9% of PVT, 22.0% of trans-diadduct, 3.2% of gem-diadduct and 1.2% of tris-(o-tolyl)phosphine.

(d) Coupling using Low Catalyst Level; Aqueous DMF; Triethylamine

The reaction is carried out as in (b), using as catalyst 0.098 g of palladium (II) acetate and 0.53 g of tris-(o-tolyl)phosphine. The contents of the reactor are sampled at 3, 5, 11, 13, 16, 22 and 25 h. Conversions are 29, 42.1, 53, 56.8, 58.5, 59.2 and 59.2%, respectively. Yields of OVT (GC) are 26.4, 37.7, 46.7, 50, 51.3, 51.6 and 51.5%, respectively.

An additional charge of catalyst (0.098 g of palladium acetate, 0.53 g of tris-(o-tolyl)phosphine is added to the reaction mixture, which is heated to 120° C. and repressurized with ethylene to 13.6 atm, gauge. The contents of the reactor are analyzed after 2, 18 and 21 hours' further heating. The yield of OVT (GC) is 62.8, 78.9 and 78.0%, respectively. Conversion of o-bromotoluene is 72, 98.5 and 99.5%, respectively.

The washed, crude product weighed 210.3 g. This polymerized partially. Monomer (103.3 g) is recovered by flash distillation.

(e) Coupling of o-Bromotoluene, Aqueous DMF; Triethylamine; Low Temperature; High Pressure The reaction is run as in (b), using a reactor temperature of 75° C. and ethylene pressure of 13.6 atm, gauge. The contents of the reactor are sampled at 3, 5, 7.25, 9, 10, 14, 16, 18 and 20 h, at which times the content of OVT (GC) is 33, 60, 77, 84.4, 87.6, 90, 91, 91.2 and 91.2%, respectively. The 20-h sample contains no detectable bromotoluene by capillary GC, of which the detection limit is 0.02%.

The rinsed, crude product weighs 239.5 g.

EXAMPLE 10

Coupling of 4-Bromobenzocyclobutene with Vinyltoluene in Aqueous DMF; Picoline

To a 100-mL flask, equipped with a magnetic stirring bar, thermowell and condenser, are charged 0.0122 g of palladium acetate, 0.0664 g of tris-(o-tolyl)phosphine, 10.0 g of bromobenzocyclobutene, 6.44 g of commercial grade m/p-vinyltoluene, 10.17 g of 2-picoline, 25 mL of N,N-dimethylformamide and 12.5 g of HPLC grade water. The system is purged with nitrogen and then heated to about 95° C. for 24 h. GC analysis shows only a trace of addition product.

EXAMPLE 11

(a) Coupling of 4-Bromobenzocyclobutene with 1,1'-Divinyltetramethyldisiloxane

To a 250 mL-round bottom flask, equipped with magnetic stirrer and reflux condenser, are charged 10.0 g of 4-bromobenzocyclobutene, 5.08 g of 1,1'-divinyltetramethyldisiloxane, 11.0 g of triethylamine, 0.0246 g of palladium (II) acetate, 0.134 g of tris-(o-tolyl)phosphine, 25 mL of deionized water and 50 mL of DMF. The reactor is purged with nitrogen for 30 min at room temperature and then heated under reflux for 20 h. GC analysis shows that all of the BrBCB is reacted.

At the end of 24 h under reflux, the reaction mixture contains 5.3% of 4-vinylbenzocyclobutene, 9.6% of 1-[(4-benzocyclobutenyl)vinyl]-1'-vinyltetramethyldisiloxane, 17.4% of 1,2-bis-(4-benzocyclobutenyl)ethylene and 48.1% of 1,1'-bis-[(4-benzocyclobutenyl)vinyl] tetramethyldisiloxane.

This experiment shows that increasing the amount of mixed solvent has little effect on the reaction.

(b) Scaled-up Coupling of 4-Bromobenzocyclobutene and 1,1'-Divinyltetramethyldisiloxane A 22-L reactor is prepared for the reaction by turning on nitrogen, introduced through a bubbler; turning on water for a reflux condenser; checking that dump valves at the bottom of the reactor are closed; charging reagents to the reactor; turning on the agitator. Nitrogen is passed through the liquid charge for 30 min. The heating cycle is initiated at this point and the temperature is checked after 45 min-1h.

A typical reactor charge is:

| | |
|---|---|
| 3200 g | 4-BrBCB (2177 mL, Dow) |
| 1626 g | 1,1'-divinyltetramethyldisiloxane (Dow Corning |

|         |                                                                                                      |
|---------|------------------------------------------------------------------------------------------------------|
|         | X1-2297 fluid)                                                                                       |
| 1755 g  | triethylamine (Fisher Scientific, Reagent Grade, 99%)                                                |
| 43 g    | tris-(o-tolyl)phosphine (Strem Chemical Co.)                                                         |
| 8 g     | palladium (II) acetate (Engelhard, 47.4% Pd)                                                         |
| 2557 g  | potassium acetate (Fisher Scientific, certified ACS)                                                 |
| 4800 mL | DMF (4000 mL to reactor; 800 mL to rinse in catalyst mixture, Fisher Scientific, ACS)                |
| 2400 mL | deionized water                                                                                      |

The reactor temperature is controlled to about 94°–97° C. for the duration of heating under reflux. At the end of 24 h, the reaction mixture is checked by GC for unreacted BrBCB, using a capillary GC 5890 apparatus. The column used (from J & W Scientific Co., Anspec, Ann Arbor, Mich. 48107), comprises a 15 meter wide bore capillary column, bonded with DB-5, having a film thickness of 1 micrometer. A flame ionization detector (HP 5890), integrator (HP 3392A) and autosampler (HP 7671A) are used. The retention time for BrBCB is 1.65 min, for DVS-BCB monoadduct 8–10.5 min, for trans-1,2-bis-(benzocyclobutenyl)ethylene about 16 min and for DVS-BCB$_2$ about 18.9–20.3 min.

If the BrBCB content is above about 2%, the reaction is continued and samples are taken every few hours and conversion of BrBCB is rechecked. If more than 2% of BrBCB is unreacted after 48 h, an additional charge of catalyst is employed.

When 98% of the BrBCB is reacted, heating for the reactor is shut off and the contents of the reactor are allowed to cool to 70° C. over about 1.5 h. Part of the water (ca 9.5 L) is removed through a bottom dump. To the reactor is added 3 L of heptane and 10 L of deionized water and the contents of the reactor are stirred for 15 min and allowed to settle. Part of the water layer is removed through a bottom dump.

An additional 10 L of deionized water is added and the contents of the reactor are stirred for 15 min and allowed to settle. Part of the water layer is removed, as above.

To the reactor are added 10 L of deionized water and 500 mL of 5N hydrochloric acid. The resulting mixture is stirred for 15 min and allowed to settle. Part of the water layer is removed, as above.

Deionized water (10 L) is added and the mixture is stirred for 15 min and allowed to settle. The pH of the mixture is checked. Part of the water is removed.

Another portion of deionized water (10 L) is added. The mixture is stirred for 10 min and allowed to settle. The pH is checked. Part of the water layer is removed. If pH is more acidic than 6–7, the contents of the reactor are washed with further portions of water. Otherwise the upper product layer is removed.

The product layer is filtered using a Fisherbrand 1-L membrane filter assembly with a 5-micron nylon filter, covered with 90 g of silica (Davison Chemical, Chromatographic Grade 62, 60×200 mesh) and 0.635 cm of magnesium sulfate, covered with glass wool. The crude filtrate is collected and chromatographed on a column (6.35 cm inner diameter, 106.68 cm in length), filled with 1200 g of silica in heptane. The excess heptane is removed from the column, which is not permitted to run dry. The effluent from the column is evaporated, using a rotary evaporator. The yield of DVS-BCB$_2$ can be determined at this point, using a Hewlett-Packard 5890 gas chromatograph with a Hewlett-Packard 7671A auto-sampler and H-P 3392A integrator, using a J & W 15-meter wide-bore capillary column bonded with DB-5, 0.10 micrometer film thickness. The temperature program is: isothermal at 50° C. or 70° C. for 2 min, ramp at 8° C. to 230° C., hold at 230° C. for 8 or more min.

The residual product is treated with aqueous hydrogen peroxide, as above.

Chromatography on silica gel can be repeated and the heptane eluant can be removed, using a rotary evaporator.

The products are analyzed at this point by GC analysis for DVS-BCB$_2$, by neutron activation analysis for Cl, Br, P, Na, K and Pd and by LC analysis for higher molecular weight components.

The yield, after 26 hours' heating, is 76.6% of DVS-BCB$_2$. This experiment shows that the reaction can be scaled up without decreasing the yield.

EXAMPLE 12

Reaction of Ethylene with o-Bromotoluene; Triethylamine; DMF; Comparative Example To a 2-L reactor (Example 9) is charged 1.214 g of palladium acetate, 6.631 g of tris-(o-tolyl)phosphine, 380.5 g of o-bromotoluene, 448.4 g of triethylamine and 873.2 g of N,N-dimethylformamide. The reactor is closed, attached to the stirrer and purged once with nitrogen and three times with ethylene. The reactor pressure is set and held at 5.78 atm (gauge) and the contents of the reactor are heated to 95° C. After 18.7 hours' heating, over 95% of the bromotoluene has reacted. The final product contains 2.75% of bromotoluene, 86.8% of o-vinyltoluene and 8.2% of bisarylation products (as GC area %).

EXAMPLE 13

Reaction of m/p-Divinylbenzene with 4-Bromobenzocyclobutene; Aqueous DMF; Triethylamine To a 5-L, round-bottom flask, fitted out with a heating mantle, bottom dump valve, thermowell, stirrer assembly and reflux condenser, is charged 0.62 g of palladium acetate, 3.35 g of tris-(o-tolyl)phosphine, 500 g of 4-bromobenzocyclobutene, 551.5 g of triethylamine, 712.5 g of fresh commercial 80% m/p-divinylbenzene, 1000 mL of N,N-dimethylformamide and 500 mL of deionized water.

The reactor is degassed with nitrogen and heated to about 92°–94° C. At the end of 5 hours' heating, a sample contains 0.06% of 4-BrBCB. The reactor is held at temperature for 23 h, at the end of which polymer buildup on the reactor walls, is observed. A sample of the liquid phase contains 0.05% of BrBCB, 49.16% of divinylbenzenes (DVB) and 41.4% of trans-bis-[(4-benzocyclobutenyl)vinyl]benzene (trans-DVB-BCB).

The reactor is cooled and 2 L of toluene are added. The water layer, which separates, is discarded. The organic layer is washed with three 1.5-L portions of deionized water, with 200 mL of 5N HCl in 1300 mL of deionized water and with two further 1.5-L portions of deionized water.

The organic phase is filtered through 150 mL of silica, topped with 40 g of magnesium sulfate, on a 5-micron membrane filter. Toluene is stripped from the filtrate at 70° C. under full vacuum to yield 226.8 g of crude product. After two days' standing in a refrigerator, 25.5 g of solid material is removed by filtration. The filtrate contains 59% of DVB and 37% of DVB-BCB. The solid contains 9.6% of DVB, 66% of DVB-BCB and 21% of bis-[(4-benzocyclobutenyl)vinyl]benzene (DVB-BCB$_2$) (LC). The liquid is distilled in a short path molecular distillation apparatus at 135° C./1 micron. The overheads fraction (66.85 g) contains 93.26% of DVB-BCB mixed isomers and 5.86% of DVB (LC).

EXAMPLE 14

Reaction of Bromobenzocyclobutene with Divinyl(dimethylsiloxane) Oligomers (a) To a 1-L round-bottom flask, fitted out with a magnetic stirrer, heating mantle, reflux condenser and temperature controller, is charged 94 g of 4-bromobenzocyclobutene (0.51 mol), 150 g of alpha,omega-divinyl(dimethylsiloxane) oligomers (Petrarch Systems, average mol. wt. 720, 0.20 mol), 58.6 g of triethylamine (0.58 mol), 42.2 g of potassium acetate (0.43 mol), 0.194 g of palladium acetate (0.864 mmol), 1.053 g of tris-(o-tolyl)phosphine (3.46 mmol), 250 mL of N,N-dimethylformamide and 125 mL of deionized water.

The contents of the flask are purged with nitrogen for 30 min and then heated to 92° C. for 22 h. Additional 4-bromobenzocyclobutene (7.5 g) is added and heating is continued. At the end of 44 h, 7.5 g of additional 4-bromobenzocyclobutene and 15.0 g of triethylamine are added to the reaction mixture. Heating is continued for a total of 68 h.

The crude reaction mixture is poured into a 2-L separatory funnel, containing 1 L of deionized water. The bottom phase is removed and toluene (200 mL) is added to the organic layer. The organic layer is washed with four 1-L aliquots of deionized water, with 50 mL of 1N HCl in 950 mL of deionized water and with four 1-L aliquots of deionized water. The organic layer is filtered through a membrane filter, packed with silica gel layer (2.54 cm) and a magnesium sulfate layer (2.54 cm). The filtrate is concentrated by a rotary evaporator at 65° C. to remove most of the solvent and at 100° C. under high vacuum for 2 h. The weight of recovered product is 199.6 g.

After two days' standing at room temperature trans-1,2-bis-(4-benzocyclobutenyl)ethylene precipitates and is recovered by filtration (5 g). The mother liquors are passed through a column of silica gel (4.445 cm id × 34.925 cm high), using heptane as eluant. Solvent was removed from the eluate using a rotary evaporator. The residue weighs 147 g.

The residue is charged to a 1-L round-bottom flask fitted out with a magnetic stirring bar. Heptane (150 mL) and methanol (75 mL) are charged to the flask. The mixture is stirred during the addition of 50-mL of 30% hydrogen peroxide in 10-mL portions over 30 min. The mixture is stirred at room temperature overnight. The mixture is washed with four 1-L aliquots of deionized water and dried over magnesium sulfate. The solution is passed through a column (4.445 cm id × 46.99 cm high), packed with silica gel. The product is washed from the column with heptane. The solvent is removed using a rotary evaporator. The residue, weighing 136.7 g, is devolatilized with a wiped-film still at 100° C./70 microns Hg. The recovered bottoms fraction is devolatilized at 110° C./21 microns Hg. The product weighs 108.5 g and contains only traces of 4-bromobenzocyclobutene (GC).

(b) The same reaction is performed, using a mixture of vinyl-terminated dimethylsiloxane oligomers (mol wt 400–700, 4–10 dimethylsiloxane units). The product is recovered as above. The infrared spectrum of the bis-[(4-benzocyclobutenyl] vinyl)dimethylsiloxane oligomers is:

| Frequency | Assignment |
| --- | --- |
| 2975 cm$^{-1}$ | C—H stretch, methyl, dimethylsiloxane |
| 2840 | C—H stretch, methylene, benzocyclobutene |
| 1615 | quadrant stretching mode, benzocyclobutene |
| 1585 | quadrant stretching mode, benzocyclobutene |
| 1480 | ring stretching mode, benzocyclobutene |
| 1265 | C—H symmetric deformation, Si-methyl |
| 1205 | benzocyclobutene ring stretch (C—H out of plane deformation) |
| 1030 | Si—O—Si stretch |
| 995 | trans-olefin C—H out-of-plane stretch |
| 850 | Si-methyl rocking mode |
| 805 | Si-methyl rocking mode |

EXAMPLE 15

Experiments are run as in Example 1, as follows:

| Olefin | Halide | Base | Solvent |
| --- | --- | --- | --- |
| VT | 4-BrBCB | Bu$_3$N | DMF/water 2:1 v/v |
| ST | 4-BrBCB | Et$_3$N | DMF/water 1:1 |
| ST | 4-BrBCB | Bu$_3$N | DMF/water 2:1 |
| AN | 4-BrBCB | Et$_3$N | DMF/water 3:1 |
| VT | 4-BrBCB | Et$_3$N | NMP/water 2:1 |
| MA | C$_6$H$_5$CH$_2$Cl | Py | DMF/water 2:1 |

AN = acrylonitrile, ST = styrene, VT = vinyltoluene, MA = methyl acrylate

Similar results are obtained.

EXAMPLE 16

(a) Experiments are run as in Examples 3 or 4, using triphenylphosphine instead of tris-(o-tolyl)phosphine. Similar results are obtained. The catalytic species is believed to be bis(triphenylphosphine)palladium (0).

(b) Similar results are obtained, using tributylphosphine as a catalyst component.

(c) Similar results are obtained using as a catalyst component tris-(dibenzylideneacetone)dipalladium (0) and triphenylphosphine or dichloro(triphenylphosphine)palladium (II).

EXAMPLE 17

Purification of Products using an Organic Hydroperoxide (a) Coupling of 4-Bromobenzocyclobutene with Divinyltetramethyldisiloxane Coupling is carried out as in Example 9(b). The reaction is complete after 25 hours' heating at 93° C. The reaction mixture is diluted with deionized water and, after stirring is stopped, cooled to 60° C. After phase separation has occurred, the water layer is removed and discarded.

The organic layer is diluted with Isopar G. The organic phase is washed with portions of deionized water until the aqueous wash is neutral.

(b) Removal of Phosphine Residues from Product

The organic phase from (a) is stirred during the addition of 2.9 g (0.032 mol) of tert-butyl hydroperoxide. The mixture is stirred at 60° C. for 16 h and then cooled to room temperature. A filter is prepared by packing a column of suitable size with 400 g of silica gel and 90 g of magnesium sulfate, on top of a 5 micron filter. The organic solution is passed through the column and the column is washed with 500 mL of Isopar G. The eluate from the column is further processed as in Example 4.

Inorganic impurity content at various points of the purification procedure are:

| ppm | crude | filtered | distilled |
|-----|-------|----------|-----------|
| Br  | 159   | 10       | 1.9       |
| Cl  | 3     | 7        | 3.3       |
| P   | 305   | <2       | <0.3      |
| K   |       | <0.3     |           |
| Na  |       | <0.2     |           |
| Si  | 8.6   | 6.3      |           |

These results show that treatment of the crude product with an organic hydroperoxide produces a product, sufficiently pure for use in electronic applications.

EXAMPLE 18

Evaluation of Organic Oxidizing Agents for Reaction with Phosphines (a) Reaction with Butylene Oxide To a 100-mL round-bottom flask, fitted out with a magnetic stirring bar and condenser, is charged 100 g of hexane, 0.5 g (0.00164 mol) of tris-(o-tolyl)phosphine and 0.236 g (0.00328 mol) of butylene oxide. This mixture contains 99.2% of tris-(o-tolyl)phosphine and 0.37% of tri-(o-tolyl)phosphine oxide (GC analysis).

The mixture is heated at 60° C. for 82 h. The mixture contains 98.2% of tris-(o-tolyl)phosphine and 0.53% of tris-(o-tolyl)phosphine oxide.

(b) Reaction with Pyridine N-Oxide

To a 100-mL round-bottom flask, fitted out with a magnetic stirring bar and condenser, is charged 100 g of Isopar g, 0.5 g (0.00164 mol) of tris-(o-tolyl)phosphine and 0.16 g (0.00164 mol) of pyridine N-oxide. The reaction mixture contains 35.9% of tris-(o-tolyl)phosphine and 0.34% of tris-(o-tolyl)phosphine oxide (GC analysis).

The mixture is stirred and heated at 120° C. for 64 h. The reaction mixture contains 31.9% of tris-(o-tolyl)phosphine and 1.57% of tris-(o-tolyl)phosphine oxide.

(c) Reaction with m-Chloroperoxybenzoic Acid

To a 100-mL round-bottom flask, fitted out with a magnetic stirring bar and reflux condenser, is charged 100 g of methylene chloride, 0.5 g (0.00164 mol) of tris-(o-tolyl)phosphine and 0.28 g (0.00164 mol) of m-chloroperoxybenzoic acid. The reaction mixture contains 37.4% of tris-(o-tolyl)phosphine oxide and no tris-(o-tolyl)phosphine (GC analysis). The mixture is passed through a column packed with 5 g of silica gel. GC analysis of the eluate shows that all of the tris-(o-tolyl)phosphine oxide has been removed. The eluate is passed through a column packed with 5 g of basic alumina. GC analysis of the eluate shows that all of the m-chloroperbenzoic acid has been removed.

These experiments show that some oxidizing agents effectively convert a phosphine to a phosphine oxide. These experiments further show that a phosphine oxide can be absorbed on silica gel and that a peroxidic oxidizing agent can be adsorbed on alumina.

EXAMPLE 19

Coupling of Ethylene and o-Bromotoluene, DMF, Comparative Example

Experiment are run in a 10-gallon reactor, otherwise as in Example 9. Build up of a salt cake on the stirrer impedes stirring. The salt cake must be removed after each run. Sampling of the reactor is complicated by accumulation of salts in the sampling tube.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for the preparation of a vinylically-unsaturated product compound, comprising reacting a halogenated organic compound with a hydrolytically-stable, vinylically-unsaturated precursor compound in the presence of (a) a homogeneous non-sulfonated zerovalent palladium catalyst complex, (b) an organic hydrogen halide acceptor and (c) a diluent, wherein the diluent is water or an aqueous solution containing up to 95% by volume of an organic solvent and wherein water is present in an amount sufficient to dissolve salts formed during the reaction and at least some diluent water is in a second phase.

2. The process of claim 1, wherein the catalyst complex is formed from a palladium salt and an organophosphine or organoarsine.

3. The process of claim 1 wherein the catalyst complex is formed from palladium (II) acetate and tris-(o-tolyl)phosphine.

4. The process of claim 1 wherein the catalyst complex is formed from a palladium (0) complex and a triarylphoshine.

5. The process of claim 1 wherein the organic hydrogen halide acceptor is a secondary or tertiary amine.

6. The process of claim 1 wherein the organic hydrogen halide acceptor is represented by the formula $R_1R_2R_3N$ and each of $R_1$, $R_2$ and $R_3$ is selected independently from straight-chain and branched-chain alkyl of 1-8 carbon atoms and cycloalkyl.

7. The process of claim 1 wherein the organic hydrogen halide acceptor is triethylamine.

8. The process of claim 1 wherein the diluent is water.

9. The process of claim 1, wherein the diluent is water and is present in amount exceeding 100% by weight of combined halogenated organic compound, hydrolytically-stable, vinylically-unsaturated precursor compound and organic hydrogen halide acceptor.

10. The process of claim 1, wherein the diluent is an aqueous solution consisting of up to 90% by volume of an organic solvent selected from the group consisting of nitriles, alcohols, linear or cyclic saturated esters, N,N-dialkylformamides, N-alkylpyrrolidinones, alkoxyalkanols, glycol ethers, dioxane, tetrahydrofuran, tetrahydropyran or hexaalkylphosphoramides.

11. The process of claim 1, wherein the diluent is an aqueous solution of 10–90% by volume of dimethylformamide or N-methylpyrrolidinone.

12. The process of claim 1, wherein the diluent is an aqueous solution of 30–70% by volume of dimethylformamide or N-methylpyrrolidinone.

13. The process of claim 1, wherein the diluent is an aqueous solution of 30–70% by volume of dimethylformamide or N-methylpyrrolidinone and the diluent is present in an amount equal to at least 70% by weight of combined halogenated organic compound, hydrolytically-stable, vinylically-unsaturated precursor compound and organic hydrogen halide acceptor.

14. The process of claim 1, wherein the halogenated organic compound is a bromo or iodo mono- or polycyclic substituted or unsubstituted carbocyclic or heterocyclic aromatic compound or a substituted or unsubstituted benzyl chloride, bromide or iodide.

15. The process of claim 1, wherein the halogenated organic compound is a brominated benzocyclobutene represented by the formula

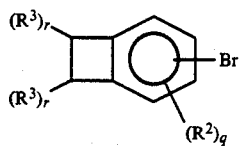

wherein $R^2$ is alkyl of 1–6 carbon atoms, alkoxy of 1–6 carbon atoms, trifluoroacetoxy, acyloxy of 1–6 carbon atoms, nitro or chloro; each $R^3$ is alkyl of 1–6 carbon atoms, aryl, nitro, chloro or cyano; q is 0, 1, 2 or 3 and each r is independently 0 or 1.

16. The process of claim 1, wherein the halogenated organic compound is 4-bromobenzocyclobutene.

17. The process of claim 1, wherein the halogenated organic compound is of the formula ArBr, wherein Ar is phenyl or o-, m- or p-tolyl.

18. The process of claim 1, wherein the halogenated organic compound is a substituted or unsubstituted benzyl chloride or bromide.

19. The process of claim 1, wherein the halogenated organic compound is a vinylic bromide.

20. The process of claim 1, wherein the hydrolytically-stable, vinylically-unsaturated precursor compound is a vinyl, allyl or methallyl organosilicon compound.

21. The process of claim 1, wherein the hydrolytically-stable, vinylically-unsaturated precursor compound is a trialkylvinylsilane, wherein alkyl is of 1–6 carbon atoms.

22. The process of claim 1, wherein the hydrolytically-stable, vinylically-unsaturated precursor compound is of the formula

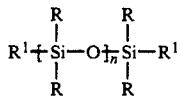

wherein each R is independently alkyl of 1–6 carbon atoms, cycloalkyl, aralkyl or aryl; each $R^1$ is independently vinyl, allyl or methallyl and n is an integer from 1 to 4500.

23. The process of claim 1, wherein the hydrolytically-stable, vinylically-unsaturated precursor compound is

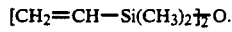

24. The process of claim 1, wherein the hydrolytically-stable, vinylically-unsaturated precursor compound is a hydrocarbon.

25. The process of claim 1, wherein the hydrolytically-stable, vinylically-unsaturated precursor compound is ethylene.

26. The process of claim 1, wherein the hydrolytically-stable, vinylically-unsaturated precursor compound is styrene.

27. The process of claim 1, wherein the hydrolytically-stable, vinylically-unsaturated precursor compound is o-, m- or p-vinyltoluene or a mixture thereof.

28. The process of claim 1, wherein the hydrolytically-stable, vinylically-unsaturated precursor compound is o-, m- or p-divinylbenzene or a mixture thereof.

29. The process of claim 1, wherein the hydrolytically-stable, vinylically-unsaturated precursor compound contains one or more of an oxygen atom, a nitrogen atom, a sulfur atom or a phosphorus atom or a combination thereof.

30. The process of claim 1, wherein the hydrolytically-stable, vinylically-unsaturated precursor compound is acrylonitrile or methacrylonitrile.

31. The process of claim 1 wherein the hydrolytically-stable, vinylically-unsaturated precursor compound is an acrylate or methacrylate ester, wherein the alcohol moiety is alkyl of 1–30 carbon atoms or substituted or unsubstituted mono- or bicyclic aryl.

32. The process of claim 1 wherein the vinylically-unsaturated product compound is a reaction product of 4-bromobenzocyclobutene and a mixture of m- and p-vinyltoluene.

33. The process of claim 1 wherein the vinylically-unsaturated product compound is a reaction product of 4-bromobenzocyclobutene and 1,1'-divinyltetramethyldisiloxane.

34. The process of claim 1 wherein the vinylically-unsaturated product compound is a reaction product of 4-bromobenzocyclobutene and an alpha,omega-divinyl(dimethylsiloxane) oligomer.

35. The process of claim 1 wherein the vinylically-unsaturated product compound is a reaction product of 4-bromobenzocyclobutene and divinylbenzene.

36. The process of claim 1 wherein the vinylically-unsaturated product compound is a reaction product of ethylene and o-bromotoluene.

37. The process of claim 1 wherein the vinylically-unsaturated product compound is a reaction product of ethylene and 4-bromobenzocyclobutene.

38. The process of claim 1 wherein the vinylically-unsaturated product compound is a reaction product of styrene and 4-bromobenzocyclobutene.

39. The process of claim 1 including a further step of treating a resulting crude product with a peroxide.

40. The process of claim 1 including a further step of chromatographing a resulting crude product over silica or alumina.

41. The process of claim 1 including the further steps of treating a resulting product with a peroxide and chromatographing the thus-treated crude product over silica or alumina.

42. The process of claim 39 wherein the peroxide is aqueous hydrogen peroxide.

43. The process of claim 39 wherein the peroxide is tert-butylhydroperoxide.

* * * * *